United States Patent [19]

Corbett

[11] 4,366,167
[45] Dec. 28, 1982

[54] β-LACTAM ANTIBIOTICS, PREPARATION AND USE

[75] Inventor: David F. Corbett, Dorking, England

[73] Assignee: Beecham Group Limited, England

[21] Appl. No.: 25,556

[22] Filed: Mar. 30, 1979

[30] Foreign Application Priority Data

Apr. 28, 1978 [GB] United Kingdom .............. 16886/78
May 6, 1978 [GB] United Kingdom .............. 18100/78

[51] Int. Cl.³ .................... A61K 31/40; C07D 487/04
[52] U.S. Cl. .............................. 424/274; 260/245.2 T
[58] Field of Search .................... 260/326.31, 245.2 T; 424/274

[56] References Cited

U.S. PATENT DOCUMENTS

| 4,162,323 | 7/1979 | Kahan | 260/326.31 |
| 4,162,324 | 7/1979 | Cassidy et al. | 260/326.31 |
| 4,163,051 | 7/1979 | Box et al. | 260/326.31 |
| 4,196,211 | 4/1980 | Christensen et al. | 260/245.2 T |
| 4,208,330 | 6/1980 | Christensen et al. | 260/245.2 T |
| 4,226,870 | 10/1980 | Christensen et al. | 260/245.2 T |

OTHER PUBLICATIONS

Morrison et al.; Organic Chemistry; pp. 526, 671–672, 927 (1969).

Primary Examiner—Mark L. Berch
Attorney, Agent, or Firm—Jacobs & Jacobs

[57] ABSTRACT

This invention provides the anti-bacterial compounds (III) and (IV):

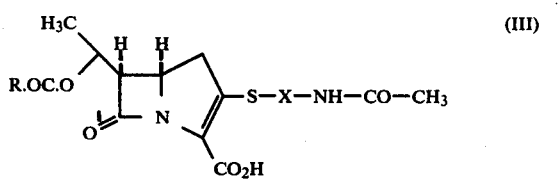

(III)

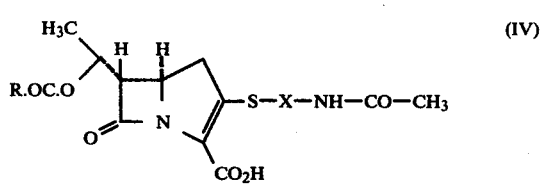

(IV)

and salts and esters thereof wherein X is a —CH₂—CH₂— or trans —CH=CH— group and R is a group $R^1$ or $NH.R^1$ wherein $R^1$ is an alkyl group of up to 6 carbon atoms, an alkenyl group of up to 6 carbon atoms, an aryl group, or an alkyl group of up to 6 carbon atoms substituted by an aryl or aryloxy group.

The invention also provides processes for their preparation comprising a the acylation or carbamoylation of the corresponding 6-(1-hydroxyethyl) compounds.

The invention further provides pharmaceutical compositions containing them.

54 Claims, No Drawings

β-LACTAM ANTIBIOTICS, PREPARATION AND USE

The present invention relates to β-lactam antibiotics, to a process for their preparation and to pharmaceutical compositions containing them.

Belgian Pat. No. 864570, West German Offenlegunsschrift No. P28 08 563.4 and U.S. Ser. No. 882,130 now abandoned all disclose inter alia the pharmaceutically acceptable salts of the compounds of the formulae (I) and (II):

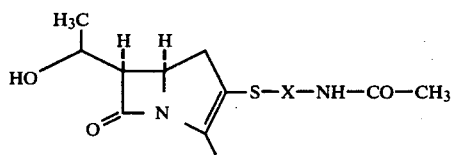

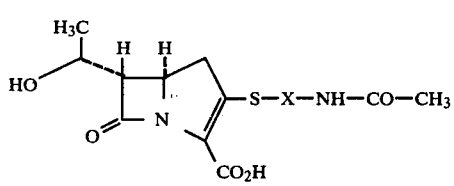

wherein X is a $CH_2CH_2$ or trans $CH\!=\!CH$ group. It has now been found that the acyl derivatives of the compounds of the formula (I) and (II) and their salts and esters are antibacterial agents.

Accordingly the present invention provides the compounds of the formulae (III) and (IV):

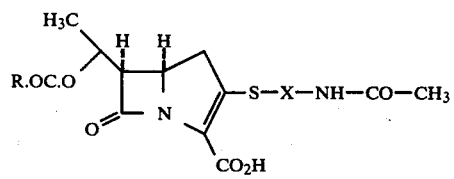

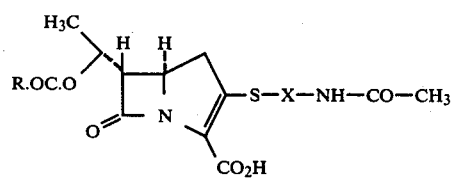

and salts and esters thereof wherein X is a $-CH_2-CH_2-$ or trans $-CH\!=\!CH-$ group and R is a group $R^1$ or $NH.R^1$ wherein $R^1$ is an alkyl group of up to 6 carbon atoms, an alkenyl group of up to 6 carbon atoms, an aryl group, or an alkyl group of up to 6 carbon atoms substituted by an aryl or aryloxy group.

The compounds of the formula (III) and their salts and esters are a particularly favoured feature of this invention in view of their particularly favourable antibacterial activity.

When used herein the term "aryl" means a phenyl group or a phenyl group substituted by an alkyl group of up to 3 carbon atoms, an alkoxyl group of up to 3 carbon atoms, a chlorine atom or fluorine atom.

Suitably R is a group $NH.R^1$. More suitably R is a group $R^1$.

Suitably the compound of the formula (III) or (IV) is provided as a salt and preferably as a pharmaceutically acceptable salt. Suitable salts include the sodium salt, the potassium salt, the calcium salt and the like.

The compounds of the formula (III) or (IV) may also be provided as esters. The esters of the compounds of the formula (III) or (IV) also possess antibacterial activity.

Suitable esters of the compounds of the formula (III) or (IV) include those wherein the ester moiety is of the sub-formula (a) or (b):

wherein $A_1$ is an alkyl group of 1-6 carbon atoms optionally substituted by an alkoxyl or acyloxyl group of 1-7 carbon atoms; $A_2$ is an alkenyl or alkynyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by a fluorine, chlorine, bromine, nitro or alkyl or alkoxyl of up to 4 carbon atoms.

Particularly suitable esters of the compounds of the formulae (III) and (IV) include the benzyl ester and substituted benzyl esters such as nitrobenzyl, for example p-nitrobenzyl.

A further particularly suitable ester of the compounds of the formulae (III) and (IV) is the phthalidyl ester.

Suitable values for $R^1$ for use in the preceding compounds include the methyl, ethyl, n-propyl, n-butyl, phenyl, benzyl, phenoxymethyl and like groups.

A particularly suitable value for $R^1$ in the preceding compounds is the methyl group.

Suitably X in the preceding compounds is a $-CH_2-CH_2-$ group.

Suitably X in the preceding compounds is a trans $-CH\!=\!CH-$ group.

The present invention also provides a pharmaceutical composition which comprises a compound of the formula (III) or (IV) or a pharmaceutically acceptable salt or ester thereof and a pharmaceutically acceptable carrier therefor.

Suitably the compositions comprise a pharmaceutically acceptable salt of a compound of the formula (III) or (IV).

Suitably the compositions comprise an ester of a compound of the formula (III) or (IV).

The compositions of this invention may be adapted for oral, topical or parenteral administration and may be used for the treatment of bacterial infections in humans or domestic animals such as infections of the respiratory and urinary tracts in humans and mastitis in cattle.

The compositions may be formulated in similar manner to that described in the aforementioned patent applications.

In general unit dosage forms of the compositions will contain from 50 to 500 mg of a compound of this invention, more usually 100 to 300 mg, for example, 125, 150, 200 or 250 mg. Such compositions may be administered once or more times a day (usually 3 or 4 times daily) so that the total daily dose is about 300 to 1000 mg for an average adult human.

The compositions for this invention may be used to treat inter alia infections due to *Staphylococcus aureus*, *E. coli* and *Klebsiella aerogenes*.

When referred to hereinbefore in each aspect it is preferred to use a compound of the formula (III) or its salt or ester rather than the compound of the formula (IV) or its salt or ester.

The present invention also provides a process for the preparation of the compounds of the formulae (III) or (IV) or a salt or ester thereof which process comprises the acylation or carbamoylation of an ester of a compound of the formula (I) or (II) and thereafter if desired when said ester is a p-nitrobenzyl ester converting the ester to a free acid or salt thereof by hydrogenation optionally in the presence of a base.

From the preceding it will be realised that one suitable aspect of this invention comprises the acylation of an ester of a compound of the formulae (I) or (II).

It will also be realised that a further suitable aspect of this invention comprises the carbamoylation of an ester of a compound of the formulae (I) or (II).

Suitable acylating agents include acid halides such as the acid chlorides, acid anhydrides and reactive derivatives produced by the reaction of an acid and a condensation prompting agent such as dicyclohexylcarbodiimide or its chemical equivalent. Such reagents may be summarised by the formula (V):

R$^1$—CO—Y           (V)

wherein Y is a readily displaceable group and R$^1$ is as defined in relation to formulae (III) and (IV).

In general an acid acceptor will be present to remove acids produced in the acylation. Suitable acid acceptors include tertiary amines such as pyridine and inorganic bases such as sodium carbonate, potassium carbonate or the like.

The acylation reaction is generally performed in an organic solvent such as pyridine, dichloromethane, tetrahydrofuran or mixtures of such solvents.

The acylation is normally carried out at a non-extreme temperature such as 0° to 30° C., for example 10°–25° C. It is frequently convenient to carry out the reaction at ambient temperature.

Suitable carbamoylating agents include isocyanates which may be summarised by the formula (VI):

R$^1$—N=C=O           (VI)

wherein R$^1$ is as defined in relation to formulae (III) and (IV).

Suitably the carbamoylation is performed under conditions similar to those already described for the acylation reaction except that an acid acceptor need not normally be employed.

When the acylation or carbamoylation reaction has been judged complete (for example as shown by tlc) the desired material may be obtained by evaporation of the solvent followed if desired by chromatographic and/or other purification processes.

If it is desired to produce a compound of the formula (III) or (IV) or a salt thereof the corresponding p-nitrobenzyl ester may be hydrogenated and thereafter neutralised with a base if a salt is desired.

The hydrogenation is normally carried out in the presence of a catalyst such as palladium, for example palladium on carbon or on some other conventional support.

Conveniently the reaction is effected using an atmospheric pressure of hydrogen at an ambient temperature although slightly elevated pressures and temperatures may also be employed if desired.

The intermediate p-nitrobenzyl esters may be prepared as described in Belgian Pat. No. 864570, German Offenlegunsschrift No. P 28 08 563.4, Japanese Patent Application No. 024375/78, and U.S. Pat. Application No. 882,130, now abandoned.

EXAMPLE 1 p-Nitrobenzyl (5R,6R)-3-[(E)-2-acetamidoethenylthio]-6-[(S)-1-acetoxyethyl]-7-oxo-1-azabicyclo[3,2,0]hept-2-ene-2-carboxylate

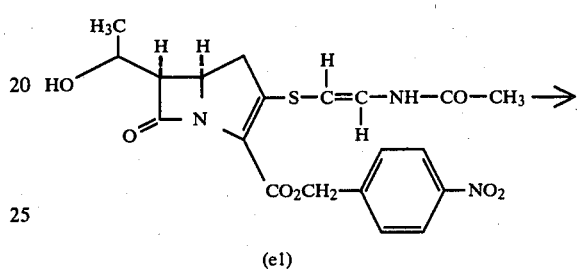

(e1)

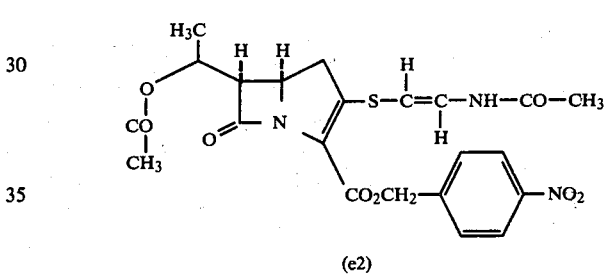

(e2)

The p-nitrobenzyl ester of the hydroxyethyl compound (e1) (200 mg) was dissolved in pyridine (2 ml) and to the solution was added acetic anhydride (0.8 ml). After 1.5 h at room temperature the solution was evaporated in vacuo and the residue chromatographed on silica gel using a gradient elution beginning with CHCl$_3$ and finishing with CHCl$_3$:EtOH (10:1). The fractions containing the product were combined and evaporated down, and the residue redissolved in CHCl$_3$ (20 ml). The solution was washed with aqueous NaHCO$_3$ solution ($\times$2) and water, before drying (MgSO$_4$) and evaporating in vacuo to afford p-nitrobenzyl (5R,6R)-3-[(E)-2-acetamidoethenylthio]-6-[(S)-1-acetoxyethyl]-7-oxo-1-azabicyclo[3,2,0]hept-2-ene-2-carboxylate (e2) as a foam (90 mg); $\nu$max. (CHCl$_3$) 3400 (br), 1780, 1735, 1700 and 1625 cm$^{-1}$; $\delta$(CDCl$_3$) 1.42 (3H, d, J 6.5 Hz, CH$_3$CH), 2.00 and 2.07 (each 3H, s, CH$_3$CO) 2.90 (1H, dd, J 17 and 10 Hz, H$_A$ of ABX, 4-CH$_A$H$_B$), 3.16 (1H, dd, J 17 and 9 Hz, H$_B$ of ABX, 4-CH$_A$H$_B$), 3.71 (1H, dd, J 6 and 9.5 Hz, 6-CH), 4.22 (1H, ca. dt J 6 and 9 Hz, H$_X$ of ABX 5-CH), ca 5.15 (1H, m, CH$_3$CH), 5.18 and 5.44 (each 1H, d, J 14 Hz, CH$_2$Ar), 5.81 (1H, d, J 14 Hz, =CH.S), 7.20 (1H, dd, J 14 and ca. 10 Hz, =CHNH), 7.6 (1H, d, J ca. 10 Hz, NH), 7.55 and 8.14 (each 2H, d, J 9 Hz, ArCH$_2$).

EXAMPLE 2

Sodium (5R,6R)-3-[(E)-2-acetamidoethenylthio]-6-[(S)-1-acetoxyethyl]-7-oxo-1-azabicyclo[3,2,0]hept-2-ene-2-carboxylate (e2) ⟶

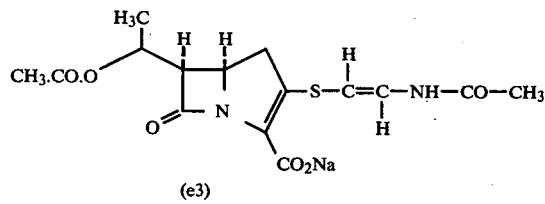

(e3)

5% Pd on C catalyst (130 mg) was suspended in a mixture of dioxan (7 ml) and water (3 ml) and the mixture was hydrogenated for 30 min. A solution of the acetate (e2) (85 mg) in dioxan (2 ml) was added to the mixture which was then hydrogenated at room temperature and atmospheric pressure for 3.5 h. The catalyst was removed by filtration over Celite, and to the filtrate was added $NaHCO_3$ (16 mg) in water (10 ml). The solution was concentrated in vacuo to a volume of about 10 ml and then washed with EtOAc (3×25 ml). The aqueous extract was concentrated to a volume of about 5 ml and then introduced onto a column (15×2 cm) of Biogel P2. Elution with water afforded the required sodium salt, the fractions being monitored by u.v. Fractions containing the product were combined and evaporated in vacuo. Addition of first ethanol and finally toluene to the residue followed by successive evaporations in vacuo afforded sodium (5R,6R)-3-[(E)-2-acetamidoethenylthio]-6-[(S)-1-acetoxyethyl]-7-oxo-1-azabicyclo[3,2,0]hept-2-ene-2-carboxylate (e3) as a cream solid (29 mgs); λmax. ($H_2O$) 308.5 and 230 nm.; νmax. (KBr) 1740–1750(br), 1680 and 1620(br) $cm^{-1}$; ($D_2O$) inter alia 1.30 (3H, d, J 6 Hz, C$\underline{H}_3$CH), 2.00 (6H, s, 2×$CH_3CO$), 3.80 (1H, m, 6-CH), 5.97 and 7.07 (each 1H, d, J 14 Hz, C$\underline{H}$=C$\underline{H}$).

The compound of this Example was found to have the following MIC values in a standard agar serial dilution test:

| | |
|---|---|
| Staph. aureus Oxford | 1.2 μg/ml |
| E. coli 0111 | 3.7 μg/ml |
| Kleb. A | <0.4 μg/ml |

EXAMPLE 3 p-Nitrobenzyl (5R,6R)-3-[(E)-2-acetamidoethenylthio]-6-[(S)-1-phenylacetoxyethyl]-7-oxo-1-azabicyclo[3,2,0]hept-2-ene-2-carboxylate (e1) ⟶

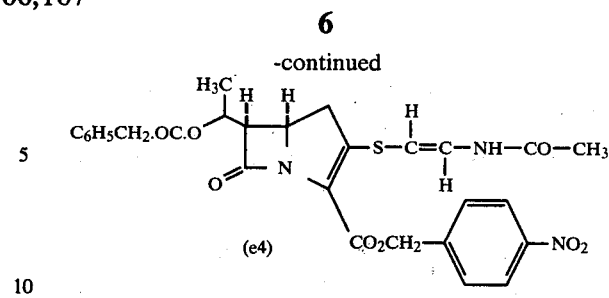

(e4)

The p-nitrobenzyl ester of the hydroxyethyl compound (e1) (65 mg) was dissolved in pyridine (1 ml). To the solution was added phenylacetyl chloride (57 μl) dropwise with stirring. Stirring at room temperature was continued for 45 minutes. The solution was evaporated in vacuo and the residue chromatographed on silica gel using EtOAc to elute. Fractions containing the required product were combined and evaporated in vacuo to afford p-nitrobenzyl (5R, 6R)-3-[(E)-2-acetamidoethenylthio]-6-[(S)-1-phenylacetoxyethyl]-7-oxo-1-azabicyclo[3,2,0]hept-2-ene-2-carboxylate (e4) as a foam (23 mg); νmax ($CHCl_3$) 1780, 1730 sh, 1700 and 1620 $cm^{-1}$.

EXAMPLE 4

Benzyl (5R,6R)-3-(2-acetamidoethylthio)-6-[(S)-1-acetoxyethyl]-7-oxo-1-azabicyclo[3.2.0]hept-2-ene-2-carboxylate

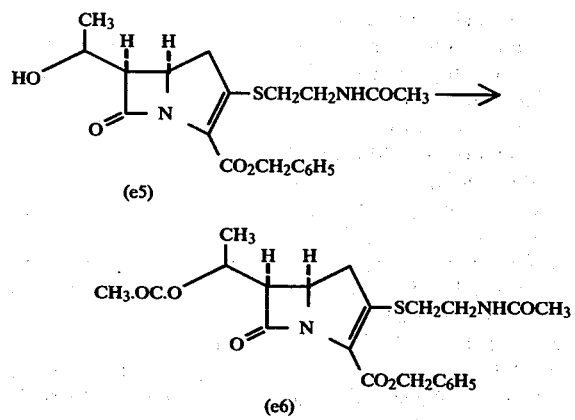

The benzyl ester of the hydroxyethyl compound (e5) (0.06 g, 0.15 mmol) was dissolved in $CH_2Cl_2$ (2 ml) containing pyridine (0.1 ml) and treated with acetic anhydride (0.05 ml). More pyridine (0.1 ml) and acetic anhydride (0.1 ml) were added after 1 hour and again after 2.5 hours. After a total of 4.5 hours at 20°, the solution was evaporated in vacuo, and the residue chromatographed to give benzyl (5R,6R)-3-(2-acetamidoethylthio)-6-[(S)-1-acetoxyethyl]-7-oxo-1-azabicyclo[3.2.0]hept-2-ene-2-carboxylate (e6) (0.017 g), as a colourless gum; νmax. ($CHCl_3$) 3450, 3300, 1780, 1740 (sh) 1705, 1670 $cm^{-1}$; λmax. (EtOH) 313 nm; δ ($CDCl_3$) 1.42 (3H, d, J 6 Hz, C$\underline{H}_3$CH), 1.93 and 2.02 (each 3H, s, 2×$CH_3CO$). 2.7-3.5 (6H, m, 3×C$\underline{H}_2$), 3.68 (1H, dd J 5 and 10 Hz, 6-C$\underline{H}$), 4.2 (1H, m, 5-CH), 5.05-5.4 (3H, m, OC$\underline{H}_2$ and $CH_3$CH), 5.85 (1H, br, NH), and 7.3 (5H, m, PhCH$_2$).

The MIC values obtained in a standard agar serial dilution test were Staph aureus Oxford=1.6 μg/ml, E. coli=6.2 μg/ml, Kleb A=1.6 μg/ml.

EXAMPLE 5 p-Nitrobenzyl (5R,6S)-3-[(E)-2-acetamidoethenylthio]-6-[(S)-1-acetoxyethyl]-7-oxo-1-azabicyclo[3,2,0]hept-2-ene-2-carboxylate

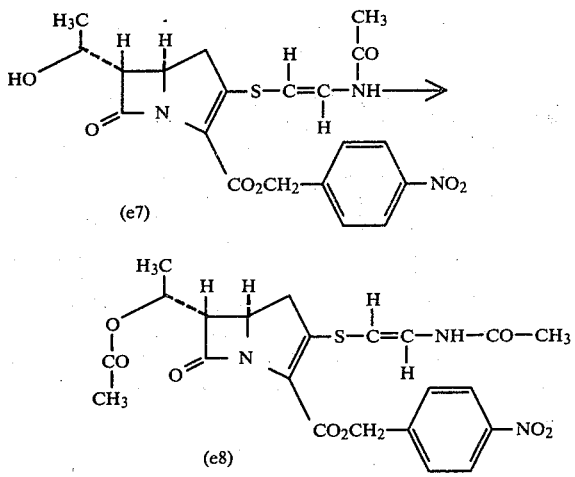

(a) The p-nitrobenzyl ester of the hydroxy compound (e7) (50 mg) was dissolved in pyridine (0.5 ml). Acetic anhydride (0.2 ml) was added and the solution was stirred at r.t. for 1.5 h. The solution was concentrated in vacuo and the residue was then chromatographed on silica gel using a gradient elution beginning with CHCl₃ and finishing with CHCl₃:EtOH (5:1). Fractions containing the required product were combined and evaporated to afford p-nitrobenzyl (5R,6S)-3-[(E)-2-acetamidoethenylthio]-6-[(S)-1-acetoxyethyl]-7-oxo-1-azabicyclo[3,2,0]hept-2-ene-2-carboxylate (e8) as a foam (38 mg); νmax (CHCl₃) 3250 (br), 1780, 1740, 1700, and 1625 cm⁻¹; δ (CDCl₃) 1.38 (3H, d, J 6 Hz, CH₃CH), 2.04 (6H, s, 2×CH₃CO), 3.05 (2H, m centre of ABX, 4-CH₂), 3.37 (1H, dd, J 3 and 3.5 Hz, 6-CH), 4.01 (1H, m. 5-CH), ca 5.15 (1H, m. CH₃CH), 5.46 and 5.18 (each 1H, d, J 14 Hz, CH₂Ar), 5.82 (1H, d, J 13.5 Hz, S.CH=) 7.18 (1H, dd, J 13.5 and 10.5 Hz, NCH=), 7.57 and 8.14 (each 2H, d, J 9 Hz, ArCH₂), and 7.83 (1H, d, J 10.5 Hz, NH).

(b) The p-nitrobenzyl ester of the hydroxy compound (e7) (50 mg) was dissolved in pyridine (1 ml) and acetyl chloride (26 mg) was added dropwise at r.t. The mixture was stirred at r.t. for 15 min and then was diluted with CHCl₃ (10 ml). The solution was washed with water (10 ml) and then dried (MgSO₄) and evaporated in vacuo. The residue was chromatographed on silica gel using EtOAc as eluant, to afford the acetate (e8) as a foam (45 mg). The product was identical to that obtained in 5(a) (T.l.c., i.r., n.m.r.).

EXAMPLE 6

Sodium (5R, 6S)-3-[(E)-2-acetamidoethenylthio]-6-[(S)-1-acetoxyethyl]-7-oxo-1-azabicyclo[3.2.0]hept-2-ene-2-carboxylate (e8) ⟶

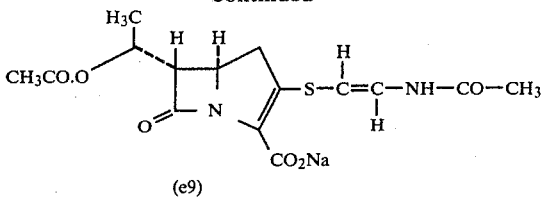

5% Pd on C catalyst (150 mg) was hydrogenated in a mixture of dioxan (7 ml) and water (3 ml) for 0.5 h. A solution of the ester (e8) (113 mg) in dioxan (2 ml) was then introduced into the catalyst mixture, and hydrogenation was continued for a further 3.5 h. The mixture was filtered over Hiflo, and NaHCO₃ (19 mg) in water (10 ml) was added to the solution which was then concentrated in vacuo to a volume of ca 10 ml. The aqueous solution was washed with EtOAc (3×50 ml), and then further concentrated in vacuo to a volume of ca 5 ml. The solution was introduced onto a column of Biogel P2 (10×2.5 cm) which was then eluted with deionised water. Fractions were monitored by u.v. and those containing the required product were combined and evaporated in vacuo. Further evaporation of ethanol and toluene from the product afforded a cream solid (51 mg) which consisted of sodium (5R, 6S)-3-[(E)-2-acetamidoethenylthio]-6-[(S)-1-acetoxyethyl]-7-oxo-1-azabicyclo[3.2.0]hept-2-ene-2-carboxylate (e9); λmax (H₂O) 309 and 229 nm, νmax (KBr) 1750 (br), 1680 and 1620 (br) cm⁻¹. δ (D₂O) inter alia 1.32 (3H, d, J 6 Hz, CH₃CH), 2.01 and 2.07 (each 3H, s, CH₃CO), 3.50 (1H, dd, J 5 and 2.5 Hz, 6-CH), 5.93 and 7.06 (each 1H, d, J 14 Hz, CH=CH).

EXAMPLE 7 p-Nitrobenzyl (5R,6S)-3-[(E)-2-acetamidoethenylthio]-6-[(S)-1-phenylacetoxyethyl]-7-oxo-1-azabicyclo[3.2.0]hept-2-ene-2-carboxylate (e7) ⟶

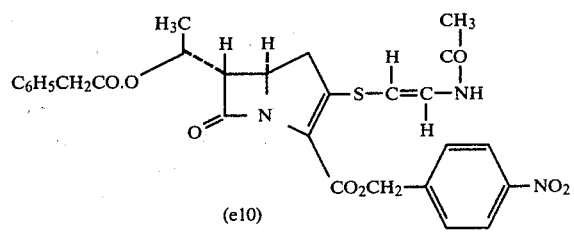

To a solution of p-nitrobenzyl ester (e7) (50 mg) in pyridine (0.5 ml) was added dropwise phenylacetyl chloride (44 μl) with stirring at r.t. Stirring was continued for 45 min and the solution then concentrated in vacuo. The residue was dissolved in CHCl₃ (0.5 ml) and the solution was immediately chromatographed on silica gel using ethyl acetate as eluant. Fractions containing the required product were combined and evaporated in vacuo to afford p-nitrobenzyl (5R,6S)-3-[(E)-2-acetamidoethenylthio]-6-[(S)-1-phenylacetoxyethyl]-7-oxo-1-azabicyclo[3.2.0]hept-2-ene-2-carboxylate (e10) as a gum (36 mg); νmax (CHCl₃) 1780, 1730(sh), 1700 and 1625 cm⁻¹; δ (CDCl₃) 1.39 (3H, d, J 6 Hz, CH₃CH), 2.05 (3H, s, CH₃CO), 2.95 (2H, m, 4-CH₂), 3.37 (1H, m, 6-CH), 3.62 (2H, s, C$\underline{H}_2$Ph), 3.87 (1H, m, 5-CH), ca. 5.20 (1H, m, CH$_3$C$\underline{H}$), 5.23 and 5.50 (each 1H, d, J 14 Hz, ArCH$_2$), 5.82 (1H, d, J 13.5 Hz, S.C$\underline{H}$=), ca. 7.15 (1H, m, NHC$\underline{H}$=), 7.25 (5H, s, PhCH$_2$), 7.61 and 8.18 (each 2H, J 9 Hz, p-NO$_2$-PhCH$_2$) and ca 7.7 (1H, br d, NH).

EXAMPLE 8

Sodium (5R,6S)-3-[(E)-2-acetamidoethenylthio]-6-[(S)-1-phenylacetoxyethyl]-7-oxo-1-azabicyclo[3.2.0]hept-2-ene-2-carboxylate (e10) ⟶

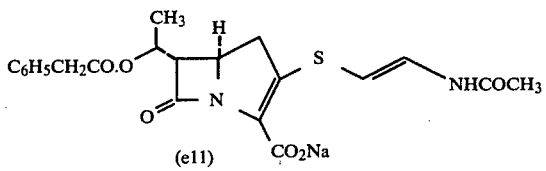

(e11)

The phenylacetate (e10) (60 mg) was dissolved in dioxan (2 ml) and the solution was added to a mixture of 5% Pd on C (90 mg) in dioxan (6 ml) and water (2 ml) which had been prehydrogenated for 0.5 h. The mixture was hydrogenated for 3 h at atmospheric pressure and room temperature and then filtered over Celite, washing well with aqueous dioxan. A solution of NaHCO$_3$ (10 mg) in water (10 ml) was added, and the solution was then concentrated in vacuo to a volume of ca 10 ml. The aqueous solution was washed with EtOAc (3×25 ml) and then concentrated in vacuo to a volume of ca 3 ml. The solution was run onto a column (10×2.5 cm) of Biogel P2 which was then eluted with water. Fractions were monitored by UV and those containing the product were combined and evaporated in vacuo. The residue was dissolved in ethanol which was then removed in vacuo and finally addition of toluene followed by further evaporation in vacuo afforded sodium (5R,6S)-3-[(E)-2-acetamidoethenylthio]-6-[(S)-1-phenylacetoxyethyl]-7-oxo-1-azabicyclo[3.2.0]hept-2-ene-2-carboxylate (e11) as a white solid (20 mg); νmax (KBr) 1740-1750 (br), 1680 and 1610 (br) cm$^{-1}$; λmax 307 and 223 nm.

EXAMPLE 9

Benzyl (5R,6S)-3-[(E)-2-acetamidoethenylthio]-6-[(S)-1-phenoxyacetoxyethyl]-7-oxo-1-azabicyclo[3.2.0]hept-2-ene-2-carboxylate

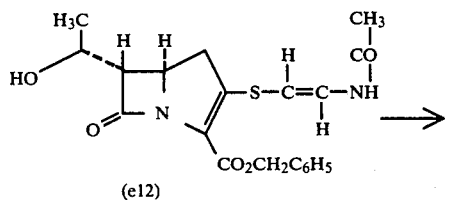

(e12)

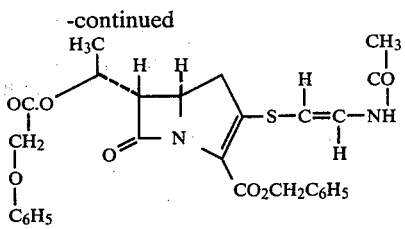

(e13)

To a solution of the benzyl ester (e12) (58 mg) in CH$_2$Cl$_2$ (3 ml) was added phenoxyacetic acid (44 mg) and pyridine (12.5 mg). The solution was cooled to 0° and a solution of dicyclohexylcarbodiimide (33 mg) in CH$_2$Cl$_2$ (1 ml) was then added. The mixture was allowed to warm to r.t. and then stirred for 2 h, before cooling to −20° and filtering off the dicyclohexylurea formed in the reaction. The filtrate was evaporated in vacuo, and the residue then chromatographed on silica-gel using EtOAc to elute. Fractions containing the product were combined and evaporated in vacuo to afford benzyl (5R, 6S)-3-[(E)-2-acetamidoethenylthio]-6-[(S)-1-phenoxyacetoxyethyl]-7-oxo-1-azabicyclo[3.2.0]hept-2-ene-2-carboxylate (e13) as a foam (39 mg); νmax (CHCl$_3$) 1780-1760 (br) 1700 and 1625 cm$^{-1}$; δ (CDCl$_3$) 1.38 (3H, d, J 6 Hz, C$\underline{H}_3$CH), 1.98 (3H, s, CH$_3$CO) ca. 2.9 (2H, m, 4-CH$_2$), 3.32 (1H, m, 6-CH), 3.88 (1H, m, 5-CH), 4.60 (2H, s, PhOC$\underline{H}_2$) ca. 5.2 (1H, m, CH$_3$C$\underline{H}$) 5.25 (2H, s, PhC$\underline{H}_2$), 5.78 (1H, d, J 14 Hz, S-C$\underline{H}$=), 6.6-7.5 (11H, m, C$_6$$\underline{H}_5$O, C$_6$$\underline{H}_5$CH$_2$ and NHC$\underline{H}$=) and 8.14 (1H, d, J 10.5 Hz, NH).

EXAMPLE 10

Benzyl (5R,6S)-3-[(E)-2-acetamidoethenylthio]-6-[(S)-1-methylaminocarbonyloxyethyl]-7-oxo-1-azabicyclo[3.2.0]hept-2-ene-2-carboxylate (e12) ⟶

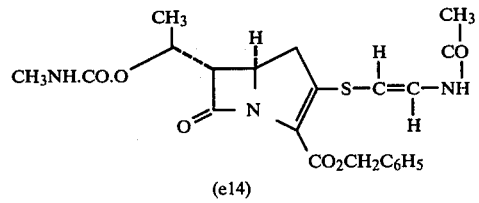

(e14)

To a solution of the benzyl ester (e12) (20 mg) in CH$_2$Cl$_2$ (1.5 ml) was added methyl isocyanate (50 μl). The solution was stirred at r.t. for 24 h and then evaporated in vacuo. The residue was chromatographed on silica-gel using a gradient elution beginning with CHCl$_3$ and finishing with CHCl$_3$:EtOH (4:1). Fractions containing the product were combined and evaporated in vacuo to afford benzyl (5R,6S)-3-[(E)-2-acetamidoethenylthio-]6-[(S)-1-methylaminocarbonyloxyethyl]-7-oxo-1-azabicyclo[3.2.0]hept-2-ene-2-carboxylate (e14) as a foam (15 mg); νmax (EtOH) 325 and 229 nm; νmax (CHCl$_3$) 3460, 3300 (br), 1780, 1700 and 1620 cm$^{-1}$; (CDCl$_3$) 1.36 (3H, d, J 6 Hz, C$\underline{H}_3$CH), 2,00 (3H, s, CH$_3$CO), 2.72 (3H, d, J 4.5 Hz, C$\underline{H}_3$NH), 2.96 (2H, m, 4-CH$_2$), 3.30 (1H, m, 6-CH), 3.97 (1H, m, 5-CH), ca 5.05 (2H, m, CH$_3$CH, NHCH$_3$), 5.25 (1H, s, C$\underline{H}_2$Ph), 5.72 (1H, d, J 13, 5Hz, S-CH=), ca 7.2 (1H, m, =C$\underline{H}$NH), 7.35 (5H, m, PhCH$_2$) and 8.14 (1H, d, J 11 Hz, NH).

EXAMPLE 11 p-Nitrobenzyl (5R,6S)-3-[(E)-2-acetamidoethenylthio]-6-[(S)-1-phenylcarbamoyloxyethyl]-7-oxo-1-azabicyclo[3.2.0-]hept-2-ene-2-carboxylate (e7) ⟶

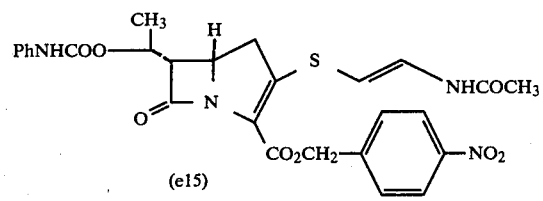

(e15)

A solution of the ester (e7) (100 mg) in pyridine (1 ml) was treated with phenylisocyanate (0.2 ml) for 1.5 h at room temperature. The solution was concentrated in vacuo and the residual solid was triturated with ether. The ether washings were discarded and the remaining solid was dissolved in chloroform and chromatographed on silica gel using a gradient elution from petroleum ether/ethyl acetate (2:3) to ethyl acetate. Fractions containing the product were combined and evaporated in vacuo. The resulting solid was triturated with ether and filtered to afford the title compound (e15) (97 mg); λmax (EtOH) 324 (16,600), 262 (17,100) and 233 (32,600); νmax (CHCl$_3$) 3440, 3340 (br), 1780, 1730 and 1700 cm$^{-1}$; δ (CDCl$_3$) 1.44 (3H, d, J 7 Hz, CH$_3$CH), 2.03 (3H, s, C$\underline{H}_3$CO), ca. 2.85-3.30 (2H, m, ABX for 4-C$\underline{H}_2$), 3.40 (1H, dd, J ca. 3 and 4 Hz, 6-CH), 4.10 (1H, m, approx. dt, J 3 and 9 Hz, 5-C$\underline{H}$), ca. 5.20 (1H, m, CH$_3$C$\underline{H}$), 5.18 and 5.46 (each 1H, d, J 14 Hz, CO$_2$C$\underline{H}_2$), 5.80 (1H, d, J 13.5 Hz, =C$\underline{H}$S), 6.95-7.45 (7H, m, =C$\underline{H}$N, and C$_6$$\underline{H}_5$N$\underline{H}$), 7.58 and 8.14 (each 2H, d, J 9 Hz, C$_6$$\underline{H}_4$NO$_2$) and 8.2 (1H, br, N$\underline{H}$CH).

EXAMPLE 12

Sodium (5R,6S)-3-[(E)-2-acetamidoethenylthio]-6-[(S)-1-phenyl-carbamoyloxyethyl]-7-oxo-1-azabicyclo[3.2.0]hept-2-ene-2-carboxylate (e15) ⟶

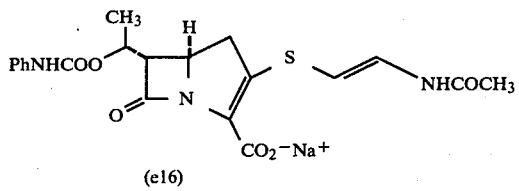

(e16)

A solution of the ester (e15) (90 mg) in 20% aqueous dioxan (5 ml) was added to a mixture of 5% Pd on C (120 mg) and 20% aqueous dioxan (5 ml) which had been prehydrogenated for 0.5 h. The mixture was then hydrogenated at atmospheric pressure and 20° for 4 h. and was then filtered through Celite. A solution of NaHCO$_3$ (14 mg) in water (10 ml) was added and the solution was concentrated in vacuo to a volume of ca. 10 ml. The aqueous solution was washed with ethyl acetate (3×50 ml), and then concentrated further in vacuo to ca. 3 ml, before admitting to a column of Bio-gel P2 (15×2.5 cm). Elution with water afforded several fractions containing the desired salt (λmax. 305 nm). The fractions were combined and the solution was evaporated in vacuo, azeotroping out water with ethanol, and ethanol with toluene to afford the title compound (e16) as a white solid (32 mg); λmax (H$_2$O) 305 (12,380) and 232 nm (22,610), νmax (KBr) 1750, 1725, 1685 and 1610 cm$^{-1}$.

EXAMPLE 13 p-Nitrobenzyl (5R,6S)-3-[(E)-2-acetamidoethenylthio]-6-[(S)-1-methylcarbamoyloxyethyl]-7-oxo-1-azabicyclo[3.2.0-]hept-2-ene-2-carboxylate (e7) $\xrightarrow{CH_3NCO}$

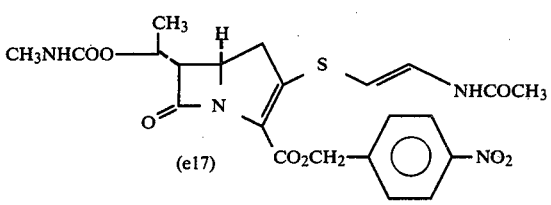

(e17)

The ester (e7) (50 mg) was dissolved in pyridine (0.5 ml) and to the solution was added methylisocyanate (0.25 ml). The solution was stirred at room temperature for 24 h and was then concentrated in vacuo. The crude product was chromatographed on silica gel using CHCl$_3$ followed by 10% EtOH in CHCl$_3$ to elute. The title compound (e17) was obtained as a gum (33 mg); νmax (CHCl$_3$) 3460, 3340 (br), 1780, 1705 and 1625 cm$^{-1}$. δ[(CD$_3$)$_2$CO] 1.34 (3H, d, J 6 Hz, C$\underline{H}_3$CH), 1.98 (3H, s, CH$_3$CO), 2.70 (3H, d, J 5 Hz, C$\underline{H}_3$NH), 3.19 (2H, d, J 8.5 Hz, 4-C$\underline{H}_2$), 3.59 (1H, apparent t, J 3.5 Hz, 6-C$\underline{H}$), 4.08 (1H, dt, J 3 and 8.5 Hz, 5-C$\underline{H}$), ca. 5.1 (1H, m, CH$_3$C$\underline{H}$), 5.27 and 5.56 (each 1H, d, J 14 Hz, CO$_2$C$\underline{H}_2$), 5.94 (1H, d, J 13.5 Hz, =C$\underline{H}$S), 6.20 (1H, br, NHCH$_3$), 7.21 (1H, dd, J 13.5 and 10 Hz, =C$\underline{H}$NH), 7.29 and 8.24 (each 2H, d, J 9 Hz, C$_6$$\underline{H}_4$NO$_2$), 9.47 (1H, br d, J 10 Hz, N$\underline{H}$CH=).

EXAMPLE 14

Sodium (5R,6S)-3-[(E)-2-acetamidoethenylthio]-6-[(S)-1-methylcarbamoyloxyethyl]-7-oxo-1-azabicyclo[3.2.0-]hept-2-ene-2-carboxylate (e17) ⟶

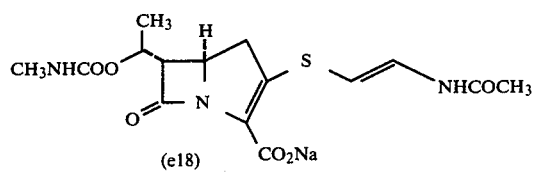

(e18)

Hydrogenolysis of the ester (e17) (80 mg) as described in Example 12 afforded the sodium salt (e18) (31 mg) as a white solid; λmax. (H$_2$O) 306 and 227 nm. νmax. (KBr) 1755, 1695 and 1610 (br) cm$^{-1}$.

EXAMPLE 15 p-Nitrobenzyl(5R,6S)-3-(2-acetamidoethylthio)-6-[(S)-1-methylcarbamoyloxyethyl]-7-oxo-1-azabicyclo[3.2.0-]hept-2-ene-2-carboxylate

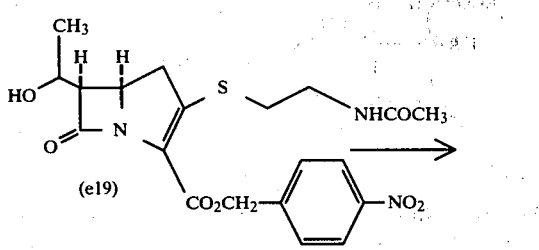

(e19)

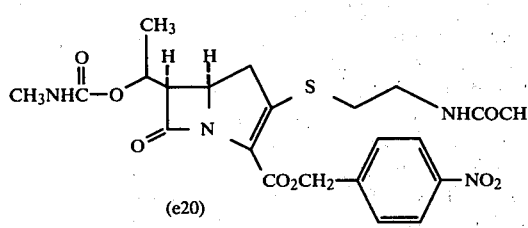

(e20)

A solution of the ester (e19) (150 mg) in pyridine (1.5 ml) was stirred with methylisocyanate (0.5 ml) for 18 h at room temperature. A white solid (47 mg) crystallised from the solution and this was obtained by filtration, washing with ethyl acetate followed by ether. The crystals consisted of the title carbamate (e20); λmax (EtOH) 316 (12,700) and 265 nm (10,900); νmax. (KBr) 1770, 1715 sh, 1695 and 1655 cm$^{-1}$. δ(d$_7$-DMF) 1.34 (3H, d, J 6 Hz, C$\underline{H}_3$CH), 1.88 (3H, s, C$\underline{H}_3$CO), 2.65 (3H, d, J 5 Hz, C$\underline{H}_3$NH), 3.05 (2H, m, C$\underline{H}_2$S), ca. 3.3–3.6 (4H, m, C$\underline{H}_2$N and 4-CH$_2$), 3.95 (1H, m, 6-C$\underline{H}$), 4.32 (1H, m, 5-C$\underline{H}$), ca. 5.10 (1H, m, C$\underline{H}$CH$_3$), 5.32 and 5.57 (each 1H, d, J 14 Hz, C$\underline{H}_2$Ar), 6.95 (1H, br, N$\underline{H}$CH$_3$), 7.82 and 8.28 (each 2H, d, J 9 Hz, Ar CH$_2$), ca. 8.1 (1H, br, N$\underline{H}$CH$_2$).

The mother liquors were concentrated in vacuo and the residue was chromatographed on silica gel employing a gradient elution from chloroform to 15% ethanol in chloroform. Fractions containing the product were combined and evaporated in vacuo, and the residue was triturated with ether to afford a further quantity (24 mg) of the title ester (e20).

EXAMPLE 16

Sodium (5R,6R)-3-(2-acetamidoethylthio)-6-[(S)-1-methylcarbamoyloxyethyl]-7-oxo-1-azabicyclo[3.2.0]hept-2-ene-2-carboxylate (e20) ⟶

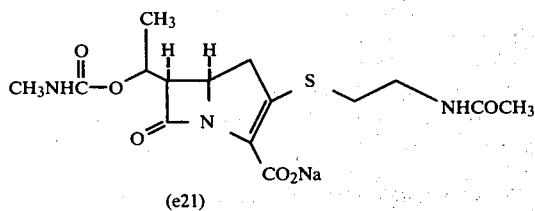

(e21)

A suspension of the ester (e20) (95 mg) in 30% aqueous dioxan was added to a mixture of 5% Pd on C (120 mg) in 30% aqueous dioxan (10 ml) which had been prehydrogenated for 0.5 h. The mixture was then hydrogenated at atmospheric pressure and room temperature for 4.5 h before adding a solution of NaHCO$_3$ (17 mg) in water (5 ml). Filtration over Celite, washing the catalyst well with water (10 ml), gave a solution which was concentrated in vacuo to a volume of ca. 15 ml. The solution was washed with ethyl acetate (3×30 ml) and then concentrated to a volume of ca. 5 ml and loaded onto a column (20×2.5 cm) of Biogel P2. Elution with water afforded several fractions which contained a u.v. chromophore at λmax. 298 nm. These were combined and concentrated in vacuo to a small volume before adding ethanol (30 ml). The solution was again concentrated to a small volume and toluene (30 ml) was added. Removal of the solvent in vacuo afforded the title salt (e21) as a cream coloured solid (49 mg). λmax (H$_2$O) 298 nm. δ(D$_2$O) inter alia 1.21 (3H, d, J 6 Hz, C$\underline{H}_3$CH), 1.83 (3H, s, C$\underline{H}_3$CO) and 2.50 (3H, s, C$\underline{H}_3$NH) (relative to HOD signal at 4.52).

The compound of this Example was found to have the following MIC values in a standard agar serial dilution test:

| | |
|---|---|
| *Staph. aureus* Oxford | 1.2 µg/ml |
| *E. coli* 0111 | 1.2 µg/ml |
| Kleb. A | 1.2 µg/ml |

What we claim is:
1. A compound of the formula:

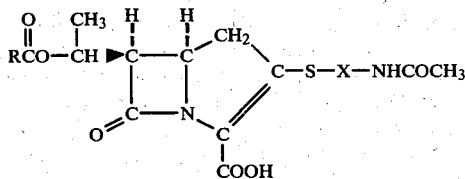

or

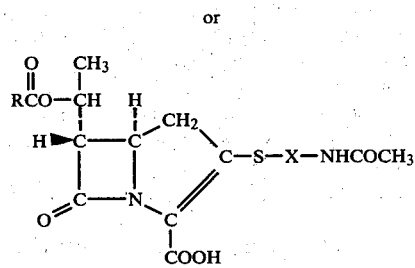

a pharmaceutically acceptable salt or benzyl, p-nitrobenzyl or phthalidyl ester thereof wherein X is trans —CH=CH— and R is R$^1$ or R$^1$NH in which R$^1$ is alkyl of up to 6 carbon atoms, alkenyl of up to 6 carbon atoms, phenyl unsubstituted or mono-substituted by alkyl of up to 3 carbon atoms, alkoxyl of up to 3 carbon atoms, chlorine or fluorine, or alkyl of up to 6 carbon atoms mono-substituted by phenyl which is unsubstituted or mono-substituted by alkyl of up to 3 carbon atoms, alkoxyl of up to 3 carbon atoms, chlorine or fluorine, or by phenoxy which is unsubstituted or mono-substituted by alkyl of up to 3 carbon atoms, alkoxyl of up to 3 carbon atoms, chlorine or fluorine.

2. A compound according to claim 1 of the formula:

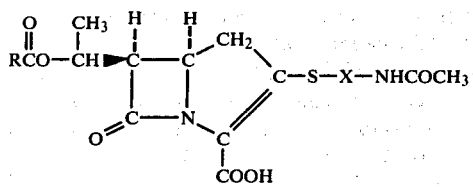

a pharmaceutically acceptable salt or benzyl, p-nitrobenzyl or phthalidyl ester thereof wherein X is trans —CH═CH— and R is $R^1$ or $R^1NH$ in which $R^1$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl which is unsubstituted or substituted by alkyl of up to 3 carbon atoms, alkoxyl or up to 3 carbon atoms, chlorine or fluorine, or by phenoxy which is unsubstituted or substituted by alkyl of up to 3 carbon atoms, alkoxyl of up to 3 carbon atoms, chlorine or fluorine.

3. A compound according to claim 2 wherein R is $NHR^1$ wherein $R^1$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl which is unsubstituted or substituted by alkyl of up to 3 carbon atoms, alkocyl of up to 3 carbon atoms, chlorine or fluorine, or by phenoxy which is unsubstituted or substituted by alkyl of up to 3 carbon atoms, alkoxyl of up to 3 carbon atoms, chlorine or fluorine.

4. A compound according to claim 2 wherein R is $R^1$, wherein $R_1$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl which is unsubstituted or substituted by alkyl of up to 3 carbon atoms, alkocyl of up to 3 carbon atoms, chlorine or fluorine, or by phenoxy which is unsubstituted or substituted by alkyl of up to 3 carbon atoms, alkoxyl of up to 3 carbon atoms, chlorine or fluorine.

5. A compound according to claim 4 wherein $R^1$ is methyl, ethyl, n-propyl, n-butyl, phenyl, benzyl or phenoxymethyl.

6. A compound according to claim 5 wherein $R^1$ is methyl.

7. A compound according to claim 1 in the form of the benzyl or p-nitrobenzyl ester.

8. A compound according to claim 1 in the form of a phthalidyl ester.

9. A compound according to claim 1 in the form of a pharmaceutically acceptable salt.

10. A pharmaceutical composition useful for treating bacterial infections in humans, domestic animals and cattle which comprises an antibacterially effective amount of a compound of the formula

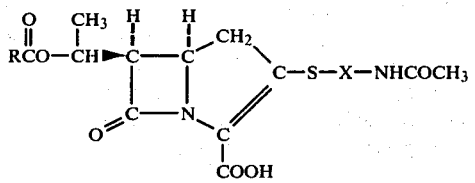

-continued
or

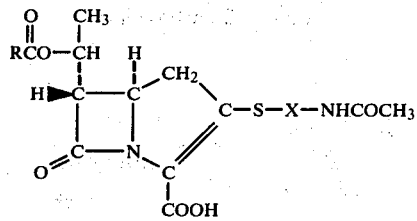

a pharmaceutically acceptable salt or benzyl, p-nitrobenzyl or phthalidyl ester thereof wherein X is trans —CH═CH— and R is $R^1$ or $R^1NH$ in which $R^1$ is alkyl of up to 6 carbon atoms, alkenyl of up to 6 carbon atoms, phenyl unsubstituted or mono-substituted by alkyl of up to 3 carbon atoms, alkoxyl of up to 3 carbon atoms, chlorine or fluorine, or alkyl of up to 6 carbon atoms mono-substituted by phenyl which is unsubstituted or mono-substituted by alkyl of up to 3 carbon atoms, alkoxyl of up to 3 carbon atoms, chlorine or fluorine, or by phenoxy which is unsubstituted or mono-substituted by alkyl of up to 3 carbon atoms, alkoxyl of up to 3 carbon atoms, chlorine or fluorine, in combination with a pharmaceutically acceptable carrier.

11. A composition according to claim 10 in unit dose form wherein each dosage unit contains from 50 to 500 mg of said compound, pharmaceutically acceptable salt or ester thereof.

12. A compound according to claim 3 wherein $R^1$ is methyl, ethyl, n-propyl, n-butyl, phenyl, benzyl or phenoxymethyl.

13. A compound according to claim 12 wherein $R^1$ is methyl.

14. A salt according to claim 9 which is the sodium, potassium or calcium salt.

15. A composition according to claim 10 wherein the compound is of the formula

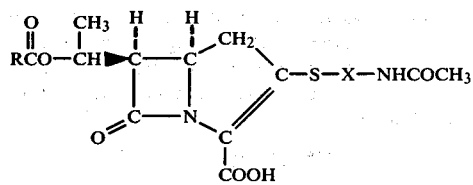

a pharmaceutically acceptable salt or benzyl, p-nitrobenzyl or phthalidyl ester thereof wherein X is trans —C═C— and R is $R^1$ or $R^1NH$ in which $R^1$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms substituted by phenyl which is unsubstituted or substituted by alkyl of up to 3 carbon atoms, alkoxyl of up to 3 carbon atoms, chlorine or fluorine, or by phenoxy which is unsubstituted or substituted by alkyl of up to 3 carbon atoms, alkoxyl of up to 3 carbon atoms, chlorine or fluorine.

16. A composition according to claim 15 wherein R is $NHR^1$ wherein $R^1$ is alkyl of up to 6 carbon atoms, alkenyl of up to 6 carbon atoms, phenyl unsubstituted or mono-substituted by alkyl of up to 3 carbon atoms, alkoxyl of up to 3 carbon atoms, chlorine or fluorine or alkyl of up to 6 carbon atoms substituted by phenyl which is unsubstituted or mono-substituted by alkyl of 3 carbon atoms, alkoxyl of up to 3 carbon atoms, chlorine or fluorine, or by phenoxy which is unsubstituted or mono-substituted by alkyl of up to 3 carbon atoms, alkoxyl of up to 3 carbon atoms, chlorine or fluorine.

17. A composition according to claim 15 wherein R is $R^1$ wherein $R^1$ is alkyl of up to 6 carbon atoms, alkenyl of up to 6 carbon atoms, phenyl unsubstituted or substituted by alkyl of up to 3 carbon atoms, alkoxyl of up to 3 carbon atoms, chlorine or fluorine, or alkyl of up to 6 carbon atoms, substituted by phenyl which is unsubstituted or substituted by alkyl of 3 carbon atoms, alkoxyl of up to 3 carbon atoms, chlorine or fluorine, or by phenoxy which is unsubstituted or substituted by alkyl of up to 3 carbon atoms, alkoxyl of up to 3 carbon atoms, chlorine or fluorine.

18. A composition according to claim 17 wherein $R^1$ is methyl, ethyl, n-propyl, n-butyl, phenyl, benzyl or phenoxymethyl.

19. A composition according to claim 18 wherein $R^1$ methyl.

20. A composition according to claim 10 wherein the compound is in the form of a pharmaceutically acceptable salt.

21. A composition according to claim 10 wherein the compound is in the form of the benzyl or p-nitrobenzyl ester.

22. A composition according to claim 10 wherein the compound is in the form of a phthalidyl ester.

23. A composition according to claim 16 wherein $R^1$ is methyl, ethyl, n-propyl, n-butyl, phenyl, benzyl or phenoxymethyl.

24. A composition according to claim 23 wherein $R^1$ is methyl.

25. A composition according to claim 20 wherein the salt is the sodium, potassium or calcium salt.

26. A composition according to claim 10 in oral administration form.

27. A composition according to claim 10 in parenteral administration form.

28. A composition according to claim 10 in topical application form.

29. The compound according to claim 1 which is

30. The compound according to claim 1 which is

31. The compound according to claim 1 which is

32. The compound according to claim 1 which is

33. The compound according to claim 1 which is

34. The compound according to claim 1 which is

35. The compound according to claim 1 which is

36. The compound according to claim 1 which is

37. The compound according to claim 1 which is

38. The compound according to claim 1 which is

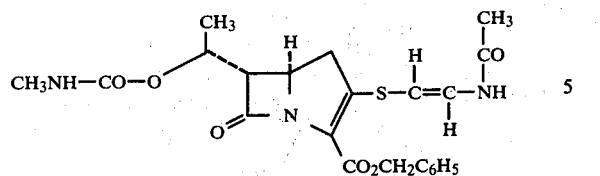

39. The compound according to claim 1 which is

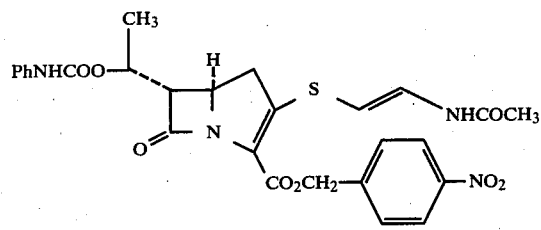

40. The compound according to claim 1 which is

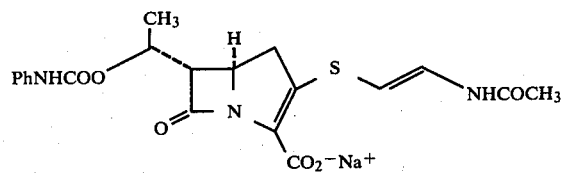

41. The compound according to claim 1 which is

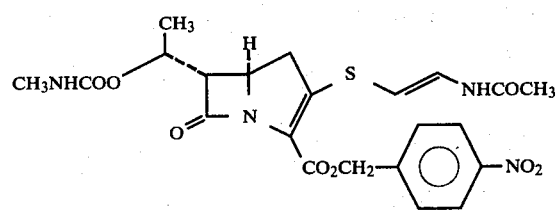

42. A composition according to claim 10 wherein the compound is

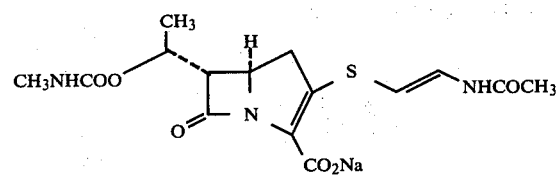

43. A composition according to claim 10 wherein the compound is

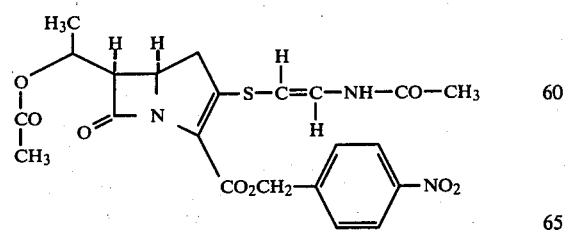

44. A composition according to claim 10 wherein the compound is

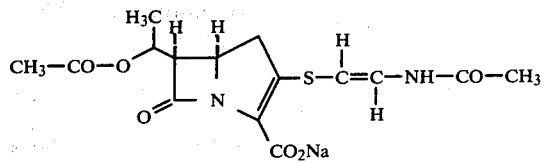

45. A composition according to claim 10 wherein the compound is

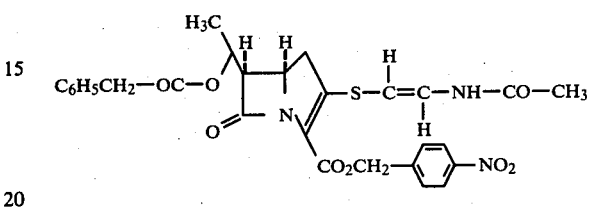

46. A composition according to claim 10 wherein the compound is

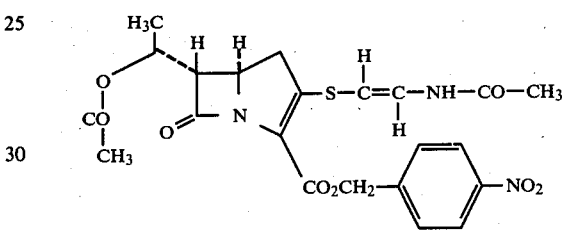

47. A composition according to claim 10 wherein the compound is

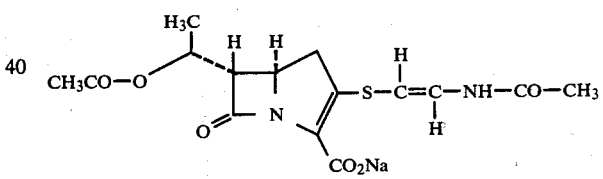

48. A composition according to claim 10 wherein the compound is

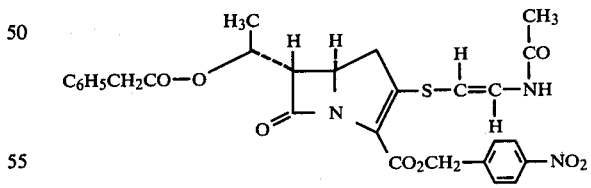

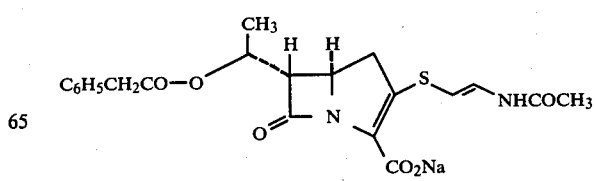

49. A composition according to claim 10 wherein the compound is
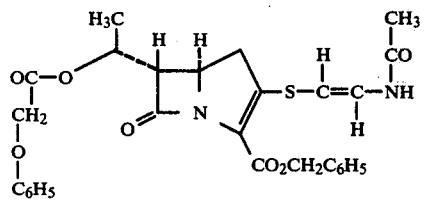
50. A composition according to claim 10 wherein the compound is
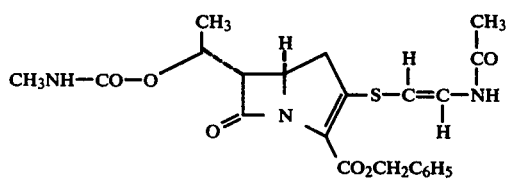
51. A composition according to claim 10 wherein the compound is
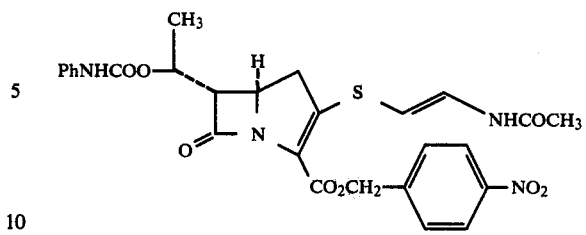
52. A composition according to claim 10 wherein the compound is
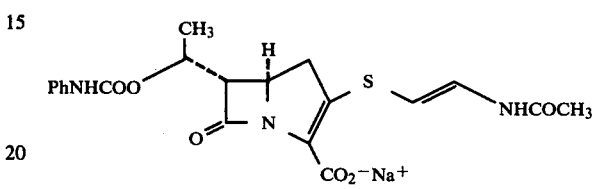
53. A composition according to claim 10 wherein the compound is
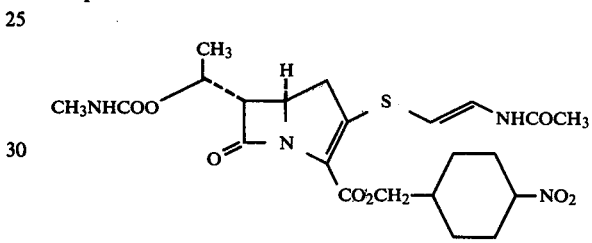
54. A composition according to claim 10 wherein the compound is
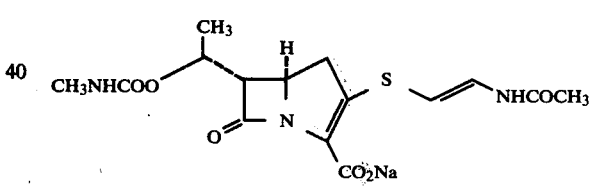
* * * * *